United States Patent [19]

Goel

[11] Patent Number: 4,855,398

[45] Date of Patent: Aug. 8, 1989

[54] REACTION OF BICYCLIC AMIDE ACETAL WITH UREA

[75] Inventor: Anil B. Goel, Worthington, Ohio

[73] Assignee: Ashland Oil, Inc., Ashland, Ky.

[21] Appl. No.: 192,987

[22] Filed: May 12, 1988

Related U.S. Application Data

[62] Division of Ser. No. 850,655, Apr. 11, 1986, Pat. No. 4,760,178.

[51] Int. Cl.$^4$ .............................................. C08G 71/02
[52] U.S. Cl. .................................... 528/367; 528/373; 528/390
[58] Field of Search ....................... 528/367, 373, 390

[56] References Cited

U.S. PATENT DOCUMENTS 4,760,178  7/1988  Goel ...................................... 564/30

*Primary Examiner*—Harold D. Anderson
*Attorney, Agent, or Firm*—John F. Jones

[57] ABSTRACT

A process for producing oligomeric compounds containing hydroxy alkyl amide groups by the reaction at a temperature in excess of about 100 degrees C. of a bicyclic amide acetal with a member selected from the group consisting of urea, biuret, thiourea, thiobiuret, alkyl substituted ureas, aryl substituted ureas, alkyl substituted thioureas, aryl substituted thioureas, alkylene ether ureas, arylene ether ureas, alkylene ether thioureas and arylene ether thioureas is disclosed.

7 Claims, No Drawings

REACTION OF BICYCLIC AMIDE ACETAL WITH UREA

This is a divisional application of copending U.S. patent application Ser. No. 850,655, filed 04/11/86 now U.S. Pat. No. 4,760,178.

This invention relates to a process for producing new compositions of matter containing hydroxy alkyl amide groups and/or hydroxy alkyl thioamide groups and to a process for preparing these new compositions by the reaction of bicyclic amide acetals with urea and related urea homologues and analogues.

The reaction of bicyclic amide acetals with ureas and related compounds has not previously been reported.

I have discovered that bicyclic amide acetals will react with ureas and related compounds to form either new monomeric or new oligomeric compounds depending on the reaction temperature used in the formation of such compounds. The monomeric and polymeric compounds produced by the process of this invention are useful in the synthesis of urethane and epoxy polymers, useful for instance in applications such as adhesives as well as in other types of chemical reactions.

The bicyclic amide acetals useful in this invention include those conforming to the Formulas I, II, or III

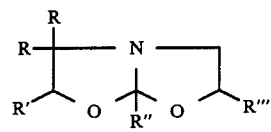

I

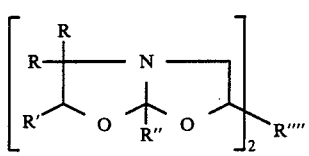

II

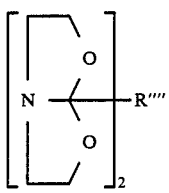

III wherein R, R', R" and R''' independently represent hydrogen, an alkyl group having from 1 to 20 carbon atoms, an aryl group having from 6 to 12 carbon atoms, an alkaryl group having from 7 to 20 carbon atoms, an alkyl ether group having from 1 to 20 carbon atoms or an aryl ether group having from 6 to 20 carbon atoms and R'''' represents an alkylene group having from 1 to 20 carbon atoms or an arylene group having from 6 to 12 carbon atoms.

The ureas and related compounds which are useful in the process of this invention include urea, biuret, thiourea, thiobiuret, alkyl or aryl substituted ureas and thioureas, alkylene or arylene ether ureas and thioureas, and the like.

The process of this invention which produces the new monomeric compositions of this invention can be illustrated in its simplest form by the following equation in which bicyclic amide acetal reacts with urea.

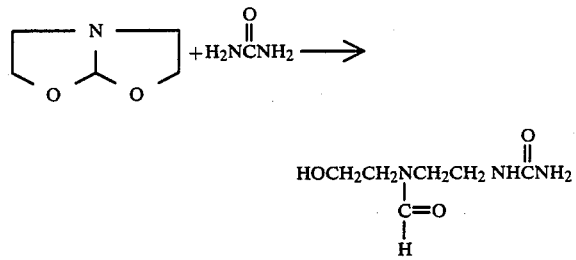

The foregoing type of reaction leading to monomeric product is carried out at a temperature in the range of from about room temperature to about 100 degrees C.

When the above described reaction is carried out at a temperature in excess of about 100 degrees C. the following occurs giving an oligomeric product along with ammonia.

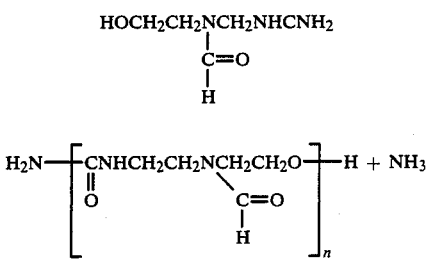

Thus, the process of the present invention can be conveniently carried out in a temperature range of from about 50 degrees C. up to about 250 degrees C. and the formation of the monomeric product proceeds at a temperature in the range of from about 50 degrees C. to just below 100 degrees C. and the formation of oligomeric products and by-product ammonia occurs at a temperature in the range of from about 100 degrees C. up to about 250 degrees C.

The process of this invention can be carried out at a pressure in the range of from about atmospheric up to about 50 atmospheres.

The process and products of this invention are further illustrated in the following representative examples.

EXAMPLE 1

A stirred mixture of 6.02 g of urea and 13 g of a bicyclic amide acetal of Formula 1 in which R, R' and R''' represent hydrogen and R" represents methyl, was heated at a temperature of about 80 degrees C. under a nitrogen atmosphere for four hours to yield a viscous liquid. Analysis of this liquid by GLC showed the complete disappearance of the starting bicyclic amide acetal and the infrared spectrum showed the presence of strong bands at 3350 cm$^{-1}$ (hydroxy group), 3200 cm$^{-1}$ (NH) and 1620 cm$^{-1}$ (amide group) showing the presence of hydroxy alkyl amide groups. The infrared spectrum also showed a weak band at 2150 cm$^{-1}$ which was probably due to the carbodiimide group.

EXAMPLE 2

A mixture of 6 g of urea and 13 g of the bicyclic amide acetal described in Example 1 was heated with stirring to a temperature of about 100 degrees C. A vigorous and exothermic reaction occurred and the reaction temperature jumped up to 160 degrees C. within five minutes with vigorous ammonia gas evolution. The evolved ammonia was estimated by dilute hydrochloric acid neutralization titration. The reaction mixture continued to become more and more viscous as ammonia was being evolved. The reaction mixture was heated for five hours at 120–140 degrees C. and during the total reaction time the ammonia evolved was determined to be about 0.9 mole per mole of urea used as starting material. The product was a very viscous material which turned to a glass when cooled to room temperature. The infrared spectrum of the product showed strong bands at 1620 cm$^{-1}$ and 1640–1720 cm$^{-1}$ (amide and urethane groups) and at 3300 cm$^{-1}$ (hydroxy and NH groups). A weak band at 2150 cm$^{-1}$ was also present.

EXAMPLE 3

The product of Example 2 (10 g) was mixed with 20 g of amido-amine containing imidazoline group (obtained from the reaction of aliphatic primary amines such as ethylene diamine with linoleic acid, 5 g of amino-ethyl piperazine, 4.5 g of bis(aminopropyl)piperazine, 5 g of poly(alkylene ether)diamine (molecular weight of 400) and 5 g of Bisphenol-A and the resulting liquid mixture was filled with 28 g of dry Kaophile filler (aluminum hydroxide modified kaolin). This product served as a hardener to cure an epoxy resin prepared by the reaction of 90 g of liquid diglycidyl ether of Bisphenol-A (epoxy equivalent weight of 180–195) with 10 g of carboxylic acid terminated butadiene/acrylonitrile (18% acrylonitrile) Hycar rubber (CTBN 1300×8 Hycar from B. F. Goodrich Co.) in the presence of 0.3% triphenyl phosphine catalyst at 120 degrees C. and filled with 24% by weight of talc filler. The epoxy resin (20 g) and hardener (15 g) were mixed and applied between two 10 inch long and 4-inch wide fiber glass reinforced sheet molding compound (SMC) panels covering a one-inch wide area. The adhesive thickness was maintained at 30 mils by adding 30 mil thick glass beads to the adhesive before application to the substrate. The adhesive test panel was cured in heated fixture at 230 degrees F. for 4 minutes followed by post curing in an oven at 285° F. for 30 minutes. One-inch wide strips were cut from the panels and lap shear strength was tested in three test procedures; (1) room temperature, (2) 180 degrees F. pull, and (3) 400 degrees F./1 hour bake and room temperature pull. All of the tests resulted in SMC fiber tear in the range of 300–700 psi.

EXAMPLE 4

The viscous liquid of Example 1 (8 g) was mixed with 10 g of an epoxy resin prepared by reacting a liquid diglycidyl ether of Bisphenol-A with 10% of butadiene/acrylonitrile (18% acrylonitrile) rubber. The mixture remained unreacted at room temperature when checked after one week. The mixture was heated on a hot plate at 130 degrees C. for ten minutes during which time some gas evolution was noticed and the mixture gelled to give a solid polymer. This shows that the product of reaction of urea with bicyclic amide acetal can be used as a latent curing agent for epoxy resins.

EXAMPLE 5

A mixture of 10.3 g of biuret and 39.1 g of the amide acetal of Example 1 was heated at 85–100 degrees C. for one hour to give a clear solution. The solution was heated further at 100 to 110 degrees C. for another two hours and the resulting solution was analyzed by GLC which showed the complete disappearance (reaction) of the starting bicyclic amide acetal. Infrared analysis showed strong broad bands at 3350 cm$^{-1}$ (hydroxy and NH groups) and 1600–1700 cm$^{-1}$ (amide and urea carbonyls). A part of this highly viscous product (10 g) was mixed with tripropylene glycol (16 g) and 0.2 g of N,N',N"-tris(dimethylamino propyl)hexahydrotriazine and the mixture was reacted with 25 g of liquid methylene bis(phenyl isocyanate) to give a solid polymer. This experient shows that the polyol product of the reaction of biuret with bicyclic amide acetal may be used in polyurethane polymer formation.

EXAMPLE 6

A mixture of 10.3 g of biuret and 26 g of the bicyclic amide acetal of Example 1 was heated with continuous stirring. When the reaction temperature reached about 100 degrees C. an exothermic reaction occured and the temperature jumped to about 170 degrees C. and some ammonia gas evolution occurred. The reaction was continued at 170 degrees C. for about 2 hours during which time ammonia gas evolution ceased and a highly viscous pasth product formed. The product became glass when cooled to room temperature. GLC analysis of the product showed the complete reaction of bicyclic amide acetal and the infrared spectrum showed strong and broad bands at 3200–3400 cm$^{-1}$ (hydroxy group), 1600–1700 cm$^{-1}$ (amide and urea group) along with a weak, sharp band at 2150.

EXAMPLE 7

The bicyclic amide acetal described in Example 1 (16 g) and 2-imidazoline (ethylene urea, 8.6 g) were mixed and heated to 165 degrees C. for seven hours. The viscosity of the liquid reaction mixture gradually increased during this time. The resulting solution was brought back to room temperature and the infrared spectrum was recorded which showed the presence of bands at 3260–3350 cm$^{-1}$ (hydroxy group) and 1620 cm$^{-1}$ (amide group). The hydroxy number of the polyol product was found to be 272.

EXAMPLE 8

A solution of 10 g of the polyol of Example 7, 16 g of propylene glycol, 5 g of dipropylene glycol, 17 g of a urethane polyol obtained from the reaction of 5000 molecular weight poly(alkylene ether)triamine with propylene carbonate in 1:3 mole ratio and 0.3 g of N,N',N"-tris-(dimethylaminopropyl)hexahydrotriazine was degassed on a rotary evaporator under reduced pressure and mixed rapidly with 100 g of degassed liquid modified methylene bis(phenyl isocyanate) to give a clear solution with 15 seconds. This solution was poured into a hot mold kept at 90 degrees C. and prepared from two mold release coated glass plates held apart by ⅛ inch thick spacers. A rapid polymerization occurred to give an opaque white polymer which was postcured at 100 degrees C. for 30 minutes. The resulting polymer sheet showed a notched izod impact strength (ASTM D-256) of 1.2 foot pounds/inch of notch and a heat distortion temperature (ASTM D-648) of 106 degrees C.

EXAMPLE 9

Following the procedure of Example 1, a mixture of 8.8 g of thiourea and 15.0 g of the bicyclic amide acetal was heated at 110° C. and an exothermic reaction occurred with the evolution of ammonia gas and the reaction mixture temperature jumped to 150° C. The reaction was continued for about two hours at 120°-140° C. and the resulting viscous liquid was analyzed by GLC and found to contain none of the bicyclic amide acetal. Infrared analysis of the product showed the presence of bands at 3360 cm$^{-1}$ (hydroxyl group), 1620 cm$^{-1}$ (thioamide group) and weak bands at 2050 cm$^1$, 2150 cm$^{-1}$ and 2200 cm$^{-1}$.

I claim:

1. The process for producing oligomeric compounds containing a member selected from the group consisting of hydroxy alkyl amide groups and hydroxy alkyl thioamide groups comprising reacting a bicyclic amide acetal with a member selected from the group consisting of urea, biuret, thiourea, thiobiuret, alkyl substituted ureas, aryl substituted ureas, alkyl substituted thioureas, aryl substituted thioureas, alkylene ether ureas, arylene ether ureas, alkylene ether thiureas and arylene ether thioureas at a temperature in excess of about 100° C.

2. The process of claim 1 carried out at a pressure of from about about atmospheric up to about 50 atmospheres.

3. The process of claim 2 wherein the bicyclic amide acetal is one having one of the Formulas I, II or III

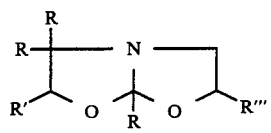

I

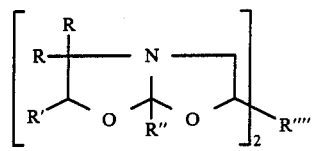

II

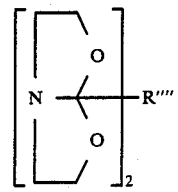

III wherein R, R', R" and R'" independently represent hydrogen, an alkyl group having from 1 to 20 carbon atoms, an aryl group having from 6 to 12 carbon atoms, an alkaryl group having from 7 to 20 carbon atoms, an alkyl ether group having from 1 to 20 carbon atoms, or an aryl ether group having from 6 to 20 carbon atoms and R"" represents an alkylene group having from 1 to 20 carbon atoms or an arylene group having from 6 to 12 carbon atoms.

4. The process of claim 3 wherein the bicyclic amide acetal is one of Formula I wherein R, R' and R'" represent hydrogen and R" represents methyl.

5. The process of claim 4 wherein the member is urea.

6. The process of claim 4 wherein the member is ethylene urea.

7. The process of claim 4 wherein the member is thiourea.

* * * * *